United States Patent [19]

McCrabb

[11] 4,037,476
[45] July 26, 1977

[54] GRAIN SAMPLING PROBE

[76] Inventor: James McCrabb, R.R. 2, West Liberty, Muscatine County, Iowa 52776

[21] Appl. No.: 697,737

[22] Filed: June 21, 1976

[51] Int. Cl.$^2$ .............................................. G01N 1/08
[52] U.S. Cl. .................................................. 73/423 R
[58] Field of Search ...................................... 73/423 R

[56] References Cited

U.S. PATENT DOCUMENTS

| | | | |
|---|---|---|---|
| 2,643,858 | 6/1953 | Hardman | 73/423 R |
| 3,683,702 | 8/1972 | O'Brien | 73/423 R |
| 3,789,671 | 2/1974 | Larson | 73/423 R |

*Primary Examiner*—S. Clement Swisher
*Attorney, Agent, or Firm*—Zarley, McKee, Thomte, Voorhees & Sease

[57] ABSTRACT

A grain sampling probe, comprised of a base, an elongated support pole, a support arm pivotally connected at one end to the top portion of the support pole, an elongated hollow probe pivotally connected to the other end of said support arm, a power output means and a mechanical drive means associated with the power output means to move the probe at a uniform rate of speed downwardly and upwardly so that the probe will obtain a truly representative core sample of the grain or other material within a grain hauling vehicle.

22 Claims, 9 Drawing Figures

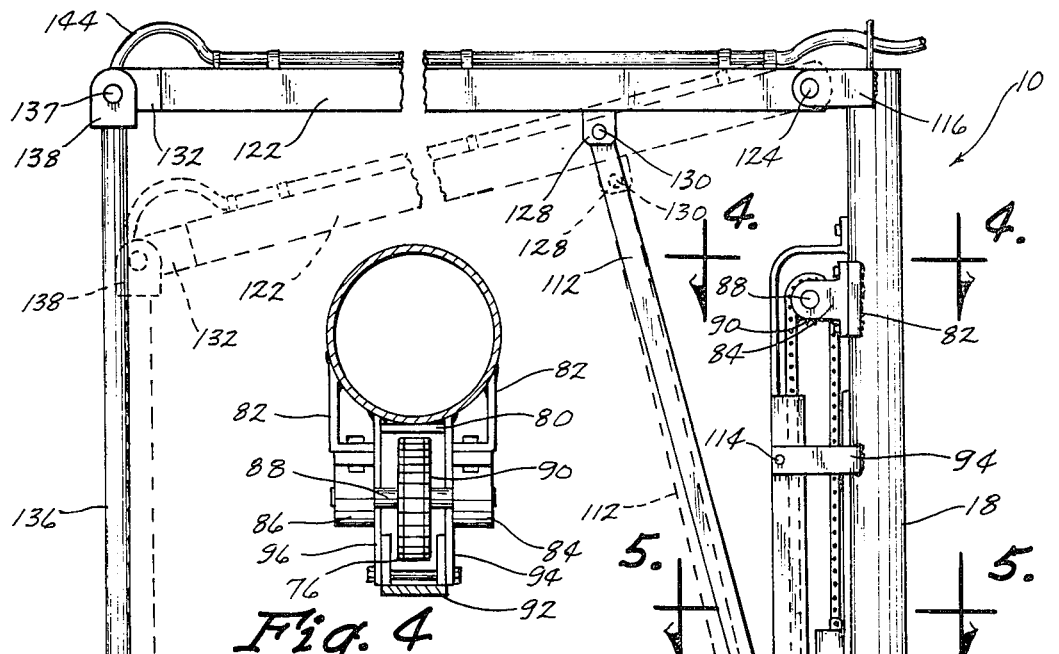
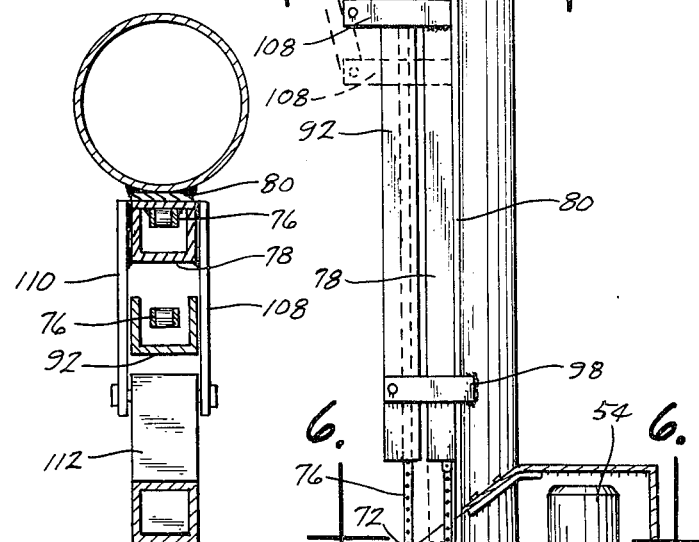
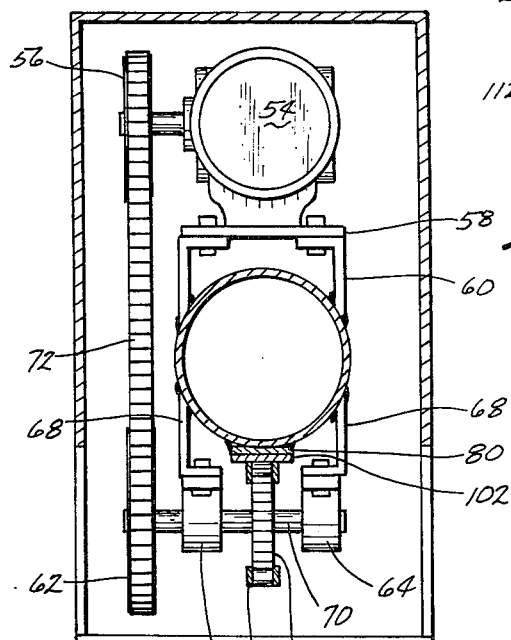
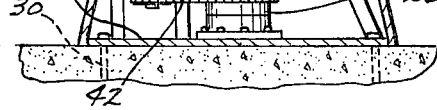

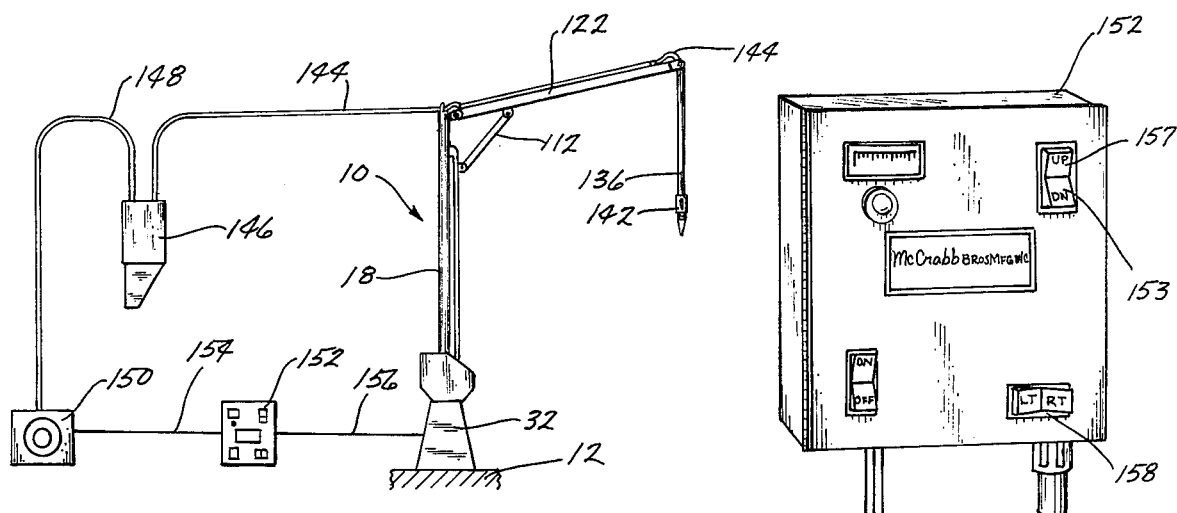
Fig. 8
Fig. 7
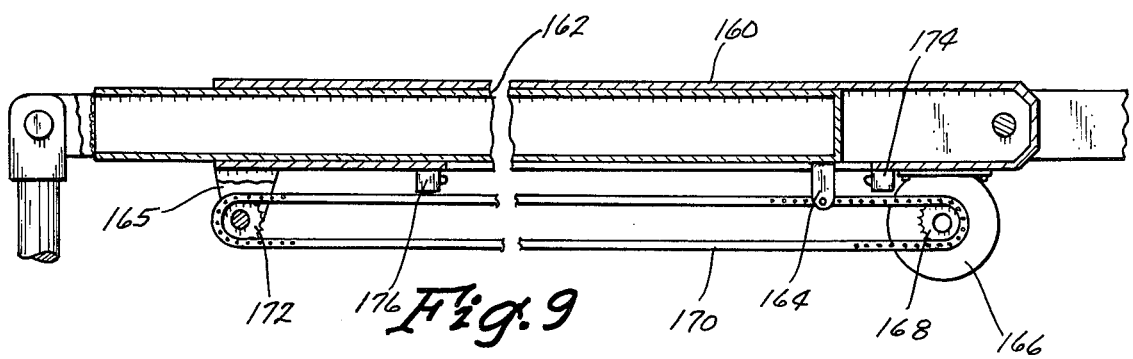
Fig. 9

GRAIN SAMPLING PROBE

BACKGROUND OF THE INVENTION

The grain hauling business is a very large business with the majority of grain, or other particulate materials being hauled by truck, railroad car or barges. Particularly for grain products, certain standards of inspection must be complied with an the price of the product is directly affected by the quality of the product. For example, the grain must have a moisture content not exceeding specified limits, the grain must not be adulterated with foreign materials to any large extent, the grain must be in good healthy condition and not rotted, and so on. Accordingly, samples are taken from the transporting vehicle in order to determine the quality of the grain in that vehicle.

Obviously, the sampling technique is only valid if the sample taken is truly representative of the grain or other particulate material contained in the hauling vehicle. Since it is not practical for the purchaser to inspect all of the grain, it is critically important that the samples which are taken are in fact truly representative in order that the quality of the hauled product can be determined.

Typically, in sampling at least two samples are taken. This is important in that a second sample can be a check on the representative accuracy of the first sample. Thus, if both samples are within reasonable limits identical, one can safely assume that the samples are a reasonably accurate representation of the entire contents of the hauling vehicle.

Experience with the hauling of grains has demonstrated that grain products often will sift and settle during shipment with the multi-fines shifting to the bottom portion of the container, with larger and bulkier materials occupying correspondingly higher positions within the particulate material load. For example, if the grain is corn, the multi-fines or smallest products typically will shift towards the bottom of the load, any foreign material such as portions of the stock and leaves will be at an intermediate position, and the larger, more bulky grain kernels will be at the top of the load. This shifting is typical for all loose particulate materials. Thus, it is important that a grain sampling probe which penetrates the load obtains a truly representative sample of every portion of the grain product through which it is penetrating. In other words, the core sample which is removed must have a respresentative amount of each type of material present at each different level within the grain load. For example, if the grain probe receives large amounts of the finest material from the bottom portion of the load, the removed core sample will be disproportionately high in fines and not be truly representative of the material in the vehicle load.

For the most part, grain sampling has been done on a commercial basis, manually. This is tedious and time consuming. Therefore, in recent years there have been some attempts at developing powered probes which can automatically sample a load of particulate material. However, heretofore such automatic sampling devices have not been able to obtain truly representative core samples of the bulk material being sampled. Therefore, automatic sampling devices have not met with a great deal of success in that they have not had the ability to duplicate the accuracy of manual sampling techniques. For example, Larson, U.S. Pat. No. 3,789,671 issued Feb. 5, 1974, relates to an automatically powered grain probe which utilizes hydraulic means to move the grain probe upwardly and downwardly within the bulk material which is being sampled. Such a device does not obtain a truly accurate sample because hydraulic powered systems will not move at a uniform rate of speed upwardly and downwardly within the bulk material.

There are several reasons why the hydraulically operated probe will not obtain a uniform sample. The bulk of the grain surrounding the probe after it is inserted into a load, causes significant resistance to the withdrawal of the probe; and, this resistance will cause eratic jerking movements of a hydraulically powered probe. Thus, when the force of the hydraulic fluid is applied against the piston of the hydraulic cylinder to cause withdrawal of the probe, typically a greater force must be applied initially in order to overcome the resistance of the grain pressing inwardly against the probe than after the probe has started movement. Therefore, there is a tendency for the probe to initially jerk rapidly through the grain sample as it is being withdrawn and thereafter to move at a slower rate of speed. As a result, since the grain sample is sucked within the probe during withdrawal, the sample that is obtained is not truly representative. Additionally, probes which are operated by hydraulic powered means during the probe withdrawal are susceptible to variance in withdrawal speed at different climatic conditions because the viscosity of the hydraulic fluid will change. As a result, hydraulic operated probes do not function very effectively in locations which are subjected to a wide variety of outdoor climactic conditions.

It is a primary object of this invention to develop a grain probe which does not utilize hydraulic means to power the probe during withdrawal from a grain load and which will obtain a truly representative core sample of a load of bulk material.

Another important object of this invention is to provide a grain probe which is powered solely by mechanical drive means in order to allow a uniform rate of withdrawal speed.

Another object of this invention is to provide a grain probe which may be installed out of doors and operate without any significant sensitivity to change in climactic conditions.

Still another object of this invention is to provide a mechanical grain probe which will obtain uniform samples regardless of the resistance caused by the inward pressing of the bulk material against withdrawal of the probe after it has been inserted into a load of material.

A still further object of this invention is to provide a probe which utilizes an extendable arm assembly in order that an operator may have greater latitude in adjustment of the lateral distance between the sampling device and a load hauling vehicle.

A still further object of this invention is to provide a sampling device which will allow better operator control to swing through an entire 180 degree arc with the ability to stop at any position within that arc in order to take a sample at any desired location within a load of particulate material.

A still further object is to provide a mechanical grain probe which exists as a free standing unit with no need for any support other than at the base of the device.

The method and means of accomplishing the results of this invention will become apparent from the detailed description of the invention which follows.

BRIEF DESCRIPTION OF THE DRAWINGS

FIG. 3 is an elevated side view, with certain parts broken away, to show the mechanical drive mechanism.

FIG. 4 is a sectional view of the probe of FIG. 3 along line 4—4.

FIG. 5 is a sectional view of the grain probe along line 5—5 of FIG. 3.

FIG. 6 is a sectional view along line 6—6 of FIG. 3.

FIG. 7 shows a control panel utilized to raise and lower the grain probe, as well as move it in a left-right swinging arc.

FIG. 8 is a schematic illustration showing the associated sample chamber, vacuum hose, vacuum motor, control panel and electrical connections.

FIG. 9 is an alternate embodiment which shows an extendable arm assembly associated with the grain probe.

DETAILED DESCRIPTION OF THE INVENTION

Figures 1, 2:
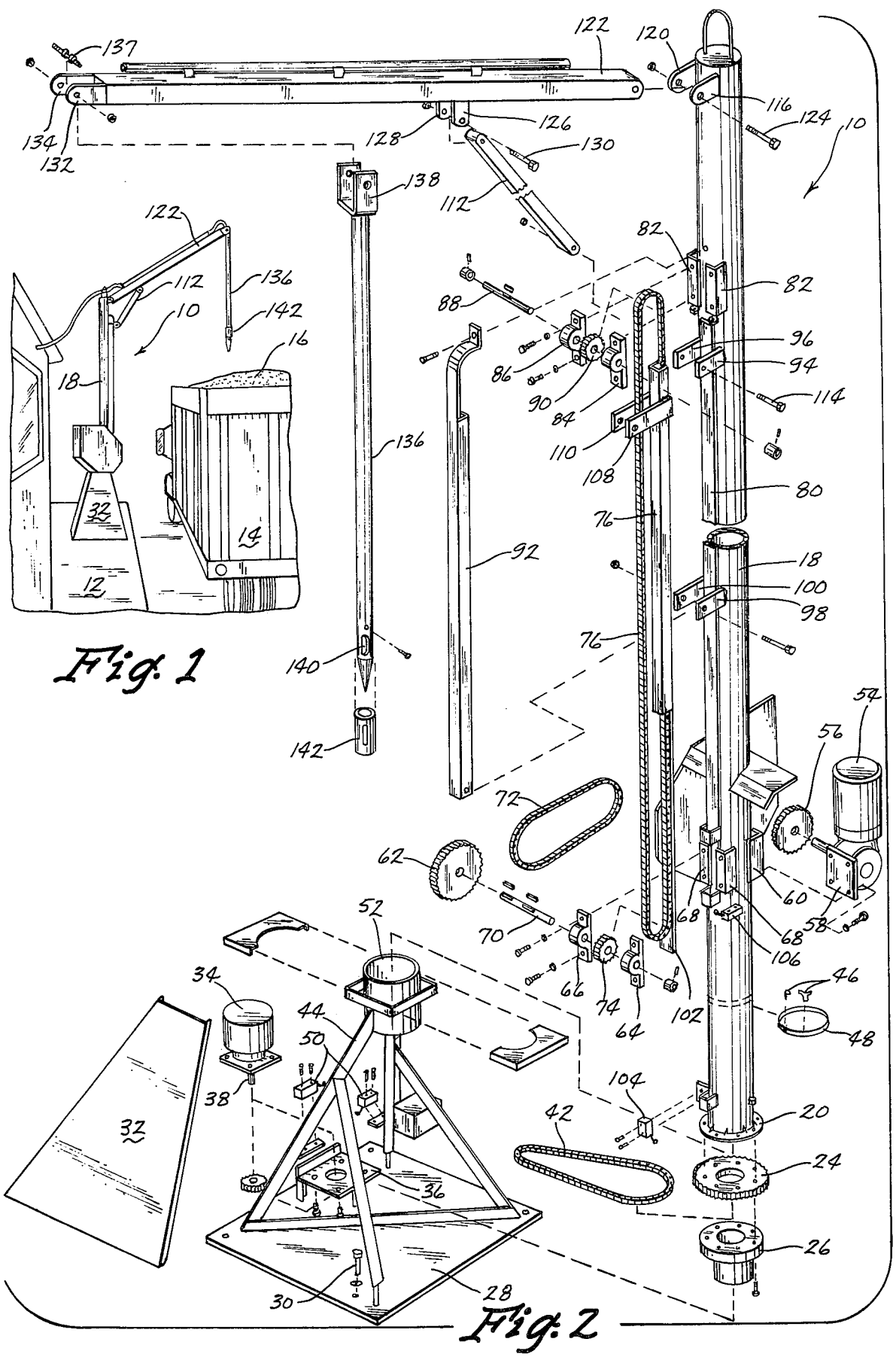
FIG. 1 shows the grain probing device of this invention in an up position with a truckload of grain, or other particulate material, ready for sampling.
FIG. 2 shows an exploded view showing the parts assembly and relationship of the grain probe device of this invention.

From time to time the term "mechanical drive means" is utilized herein. It is to be understood that by mechanical drive means, applicant refers to a drive means which contains entirely a mechanical linkage connection between a power output means and any member which is being driven by the power output means. Thus, it is to be distinguished from a hydraulic system wherein an essential part of the linkage is a fluid which applies pressure towards one member in order to move yet another mechanical member.

As will be apparent from the description below, the invention primarily lies in the mechanical drive means which allows the upward and downward movement of a probe within a load of bulk material at a uniform rate of speed in order to allow withdrawal of a truly representative core sample of material from the bulk load. However, as those skilled in the art of automatic grain probes understand, there is associated with the probe device, a vacuum means in order to create suction to draw a sample of bulk material into the probe, a vacuum motor in order to create the suction means, a control panel in order to control the upward and downward movement of the probe and associated electrical connections. These will be briefly described, hereinafter, with reference to FIG. 9.

FIG. 1 shows the grain probe, referred to generally at 10, mounted on a loading dock 12 with a vehicle 14 filled with bulk material 16 in a ready position for taking a sample. The grain probe 10 is shown in an up position ready for insertion and removal of a sample.

With continuing reference to FIG. 2, the device is comprised of an elongated support pole 18 having at its lower end radially outwardly extending lip 20. Mounted to lip 20 by conventional means of hub nuts 22 is right-left turning sprocket 24 and hub 26.

The base for support pole 18 is comprised of base plate 28 which may be bolted to loading dock 12 by bolts 30 as depicted, and associated covering panels 32.

Electrical motor 34 is mounted via motor mount 36 to base plate 28. Mounted to shaft 38 of motor 34 is sprocket 40. Flexible chain 42 extends around sprocket 40 and right-left turning sprocket 24. Thus, when motor 34 is operated, sprocket 40 is turned, chain 42 is moved, and associated right-left turning sprocket 24 is moved along with tower 18 to rotate tower 18 about its longitudinal axis. Motor 34 is an electrically reversible motor and can be reversed for rotation of tower 18 in the opposite direction in order to impart right-left movements thereto.

Tower 18 is supported, in the manner shown in FIG. 2 in its upright position by bracing 44 in conventional fashion.

Near the base of tower 18 are mounted conventional microstops 46 via micro-stop holding band 48. As tower 18 is rotated either in a right or left direction, microstops 46 engage micro-switches 50 in order to shut off power to motor 34. In this way the right-left movement of tower 18 can be controlled by the distance between micro-stops 46 which can be adjustably moved around tower 18.

Of course, tower 18 is rotably supported in housing 52 which is supported by bracing 44 as depicted in FIG. 2.

Mounted to tower 18, towards the lower portion thereof, is 90 degree reversible electric worm gear driven motor 54. Mounted to the shaft of motor 54 is the primary up-down turning sprocket 56. As can be seen motor 54 is mounted via plate 58 to bracket 60 on tower 18. In like manner, up-down driven sprocket 62 has bearings 64 and 66 mounted to bracket 68 positioned on support pole 18 opposite bracket 60. Driven sprocket 62 is mounted via bearings 64 and 66 via cross-shaft 70. Continuous flexible chain 72 extends around turning sprocket 56 and driven sprocket 62. Also mounted to cross shaft 70 is a smaller driven sprocket 74, which as explained hereinafter, engages push arm driving chain 76.

Push arm driving chain 76 is a continuous flexible chain and has welded within the continuous circle of the chain, rigid push arm 78. Thus, driving movement of chain 76 will cause movement of rigid push arm 78.

Mounted to the front of support pole 18 parallel to the longitudinal axis thereof, is slide plate 80. Rigid push arm 78 is placed in abutting relationship with slide plate 80, and held thereagainst in a manner hereinafter described.

Towards the top portion of support pole 18 is mounting bracket 82. Bracket 82 supports bearings 84 and 86 and cross shaft 88 which has positioned thereon driven sprocket 90. Chain guard 92 is also mounted to bracket 82 and is further supported via spaced apart ears 94 and 96 and ears 98 and 1000 with associated bolts, not specifically numbered.

Thus, as can be seen when motor 54 drives up-down turning sprocket 56, this in turn rotates driven sprocket 62 and smaller driven sprocket 74. Since sprocket 74 engages chain 76, chain 76 is driven and rigid push arm 78 is moved longitudinally, parallel to the longitudinal axis of support pole 18 as it slides upwardly and downwardly along slide plate 80 mounted to support pole 18. As can be seen, rigid push arm 78 has a flat downwardly extending portion 102. Portion 102 engages microswitch 104 which, when so engaged automatically shuts off reversible motor 54. In like manner engagement of microswitch 106 stops the upward movement of rigid push arm 78 by shutting off motor 54. Thus, the up-down movement of rigid push arm 78 is limited by microswitches 104 and 106.

Near the top portion of rigid push arm 78, are outwardly protruding spaced apart tabs 108 and 110. Pivot arm 112 is pivotally mounted via bolt 114 to tabs 108 and 110.

Adjacent the top of support pole 18 are ears 116 and 120. Support arm 122 is pivotally mounted, via bolt 124 to ears 116 and 120. In like manner, the other end of pivot arm 112 is pivotally mounted to support arm 122 via downwardly extending ears 128 and bolt 130. Thus, as seen in dotted line on FIG. 3 up-down movement of rigid push arm 78 will cause corresponding up-down movement of support arm 122.

At the other end of support arm 122, are spaced apart protruding ears 132 and 134.

Hollow probe 136 is mounted via bracket 138 and ears 132 and 134 and cross pin 137 for pivotal movement to the outer end of support arm 122. Hollow probe 136 has at its lower end, opening 140, the side of which may be controlled by movement of covering sleeve 142. In the middle of bracket 138 is an additional opening into the hollow interior portion of probe 136.

A best depicted in FIG. 3, a flexible hose or conduit 144 is placed in sealing relationship with the top opening into hollow probe 136.

FIG. 8 best depicts the relationship, in schematic illustrative form, of the entire series of components making up the complete unit. The prove device 10, as hereinbefore described, has conduit 144 which extends from the sealing relationship with the interior of hollow probe 136 into sealing relationship with receiving chamber or sample container 146. Hose 148 is also in sealing relationship with chamber 146 and with the vacuum motor, or suction means 150. Thus, motor 150, when operated, creates suction which extends through chamber 146 and via conduit 144 through probe 136. Grain is drawn through the opening 140 into the hollow interior of probe 136, through conduit 144 and into container 146. Vacuum motor 150 is connected to control panel 152 via conventional electrical connecting wires 154 reversible motors 34 and 54 via electrical connection. Vacuum motor 150 is wired to operate simultaneously with upward movement of probe 136. The control panel is shown in FIG. 7.

In actual operation, the device works as follows, assuming the probe is in an up position. The down button 153 on control panel 152 is pushed and motor 54 is actuated with driving sprocket 56 turning the via chain 72, driven sprocket 62 is turned, and in turn sprocket 74 is turned. Clockwise rotation of sprocket 74 causes rigid push arm 78 to be moved downward until it reaches the bottom of its limited movement and stops by engaging micro-switch 104 via extended arm portion 102. As rigid push arm 78 is moved downward, support arm 122 because of the pivotal linkage to pivotal arm 112, is also moved downward and correspondingly probe 136 is moved downward parallel to the longitudinal axis of support pole 18, see FIG. 3. After the downward extension of probe 136 into the interior of bulk material 16, the up or withdrawal button 157 is pushed on control panel 152. This automatically reverses motor 54 and simultaneously turns on vacuum motor 150. The chain driven probe 136 then begins a uniform rate of speed withdrawal from the interior portion of the bulk material load 16 and simultaneously a vacuum or suction is created to allow samples to be drawn into the interior of probe 136 via opening 140. When microswitch 106 is engaged, motor 54 is shut down.

In the event that probe 136 is to be moved right or left, the right or left movement button 158 on panel 152 is pushed which actuates motor 34 to cause rotation of support pole 18 in the manner described via driven sprocket 40 and right-left turning sprocket 24. Microstops 46 when they engage micro-switches 50, limit the right-left movement to the predetermined degree set by the operator. Thus, as can be seen, a device has been provided which provides for a slow uniform rate of movement of a hollow probe in order to provide a truly representative sample. Moreover, the possibility of jerking movement has been eliminated, there is no lost motion, and therefore a sample which is obtained has representative amounts of all of the material coming into contact with the opening 140 in probe 136.

FIG. 9 shows an alternate assembly for support arm 122.

In FIG. 9 a hollow arm assembly 160 has telescoped therewithin a second arm assembly 162. Arm assembly 162 has downwardly extending tabs 164 which protrude through a slot in hollow arn assembly 160. Motor 166 having sprocket 168 mounted to its shaft. Motor 166 is mounted to the underneath side of hollow arm assembly 160. Continuous chain 170 extends around sprocket 168 and sprocket 172 which is mounted to tab 165. Tab 164 is welded to chain 170. Thus, rotary movement of sprocket 168 causes telescopic extension or retraction of arm assembly 162. Microswitchs 174,176 shuts off motor 166 when it is engaged by a micro-stop associated with tab 164. Thus, as can be seen in FIG. 9 there is provided a telescopically extendable arm assembly in order to provide greater operator adjustment for the lateral distance between a vehicle and the support pole 18.

As can be seen, the invention provides a device which accomplishes all of the stated objects.

What is claimed is:

1. A grain sampling probe comprising,
a base,
an elongated support pole, mounted to said base,
a support arm having inner and outer ends, said inner end being pivotally connected to said support pole,
a vertically disposed elongated hollow probe pivotally connected to said outer end of said support arm,
a first power output means, and
mechanical drive means associated with said power output means, said support arm and said support pole to move said probe at a uniform rate of speed downwardly and upwardly.

2. The sampling probe of claim 1 wherein said support pole is mounted to said base for rotatable movement about the longitudinal axis of said support pole.

3. The sampling probe of claim 2 wherein a second power output means is associated with said support pole, and a second mechanical drive means is associated with said second power output means for rotable movement of said support pole at a uniform rate of speed.

4. The sampling probe of claim 1 wherein said power means is an electrically reversible motor.

5. The sampling probe of claim 3 wherein said mechanical drive means is comprised of a first sprocket operatively secured to said first power output means, a second sprocket operatively associated with said support pole, and a continuous flexible power connecting means embracing the peripheries of said first and second sprockets.

6. The sample probe of claim 4 wherein said mechanical drive means has third and fourth sprockets operatively associated with said support pole, said third sprocket being driven by said second sprocket, a second continuous flexible power connecting means embracing the peripheries of said third and fourth sprockets, and which is also operatively connected to said support arm, whereby movement of said second continuous flexible power connecting means causes movement of said grain probe.

7. A grain sampling probe comprising,
a base,
an elongated support pole, mounted to said base,
a longitudinally extendable support arm having inner and outer ends, said inner end being pivotally connected to said support pole,
a vertically disposed elongated hollow probe pivotally connected to said outer end of said support arm,
a first power output means, and
mechanical drive means associated with said power output means, said support arm and said support pole to move said probe at a uniform rate of speed downwardly and upwardly.

8. The sampling probe of claim 7 wherein said extendable support arm is comprised of two telescopically extendable members.

9. The sampling probe of claim 8 wherein a second power output means is associated with said extendable support arm for extension and retraction thereof.

10. The sampling probe of claim 9 wherein a second mechanical drive means is associated with said second power output means by a continuous flexible power connecting means.

11. A grain sampling probe comprising,
a base,
an elongated support pole mounted to said base,
a support arm having inner and outer ends, said inner end being pivotally connected to said support pole,
a vertically disposed elongated hollow probe pivotally connected to said outer end of said support arm, said probe having openings into the interior thereof near each end of said probe,
a grain sample container,
a suction means,
a conduit connecting said probe, said container and said suction means,
a first power output means,
mechanical drive means associated with said first power output means to move said probe at a uniform rate of speed downwardly and upwardly, and
means to activate said suction means for operative use only during upward withdrawal movement of said probe whereby a representative grain sample is sucked through said probe, said conduit and into said container.

12. The sampling probe of claim 11 wherein said mechanical drive means is comprised of a first sprocket operatively secured to said first power output means, a second sprocket operatively associated with said support pole, and a continuous flexible power connecting means embracing the peripheries of said first and second sprockets.

13. The sample probe of claim 12 wherein said mechanical drive means has third and fourth sprockets operatively associated with said support pole, said third sprocket being driven by said second sprocket, a second continuous flexible power connecting means embracing the peripheries of said third and fourth sprockets, and which is also operatively connected to said support arm, whereby movement of said second continuous flexible power connecting means causes movement of said grain probe.

14. The sample probe of claim 7 wherein said mechanical drive means is comprised of a first sprocket operatively secured to said first power output means, a second sprocket operatively associated with said support pole, and a continuous flexible power connecting means embracing the peripheries of said first and second sprockets.

15. The sample probe of claim 14 wherein said mechanical drive means has third and fourth sprockets operatively associated with said support pole, said third sprocket being driven by said second sprocket, a second continuous flexible power connecting means embracing the peripheries of said third and fourth sprockets, and which is also operatively connected to said support arm, whereby movement of said second continuous flexible power connecting means causes movement of said grain probe.

16. A grain sampling probe comprising,
a base,
an elongated support pole, mounted to said base,
a support arm having inner and outer ends, said inner end being pivotally connected to said support pole,
a vertically disposed elongated hollow probe pivotally connected to said outer end of said support arm,
a first power output means, and
chain drive means associated with said power output means, said support arm and said support pole, said chain drive means being immediately responsive to said first power output means to move said probe at a uniform rate of speed downwardly and upwardly.

17. A sampling probe of claim 14 wherein said chain drive means includes a continuous driven chain which has a push arm welded within the circle of said continuous chain, said push arm being operatively connected to said support arm, so that said support arm moves responsively to movement of said push arm.

18. A grain sampling probe comprising,
a base,
an elongated support pole, mounted to said base,
a support arm having inner and outer ends, said inner end being pivotally connected to said support pole,
a vertically disposed elongated hollow probe pivotally connected to said outer end of said support arm,
a first power output means, and
a continuous flexible power connecting means associated with said power output means, said support arm, and said support pole, said power connecting means being immediately responsive to said first power output means to move said probe at a uniform rate of speed downwardly and upwardly.

19. The structure of claim 1 wherein said mechanical drive means includes a pivot arm pivotally connected between said support arm and said pole and connecting means on said pole and support arm and opposite ends of said pivot arm for maintaining one end of said pivot arm stationary and allowing the other end to move relative to the respective longitudinal axis of said support arm and pole in response to operation of said mechanical drive means.

20. The structure of claim 19 wherein said connecting means between said support arm and said one end of said pivot arm maintains said pivot arm stationary relative to the longitudinal axis of said support arm and the connecting means between said pole and said other end of said pivot arm allows for movement of said pivot arm longitudinally of said pole.

21. The structure of claim 20 wherein said mechanical drive means includes an endless driving chain vertically positioned on said pole and connected to said other end of said pivot arm and operatively connected to said power output means.

22. The structure of claim 1 wherein said probe pivotally connected to said outer end of said support arm is further defined and including connecting means for limiting pivotal movement to a vertical plane including said support arm whereby downward forces applied to said probe by said support arm do not cause reactionary lateral forces to be applied to said support arm to move it horizontally.

* * * * *